United States Patent [19]

Guérin

[11] 3,968,155

[45] July 6, 1976

[54] PROCESS FOR PREPARED PERCHLOROMETHYL MERCAPTAN BY CHLORINATION OF CARBON DISULFIDE

[75] Inventor: Jean Guérin, Grenoble, France

[73] Assignee: Produits Chimiques Ugine Kuhlmann, Paris, France

[22] Filed: Apr. 28, 1975

[21] Appl. No.: 571,919

[30] Foreign Application Priority Data

June 21, 1974 France .............................. 74.21586

[52] U.S. Cl. .......................... 260/543 H; 260/607 R
[51] Int. Cl.² ............... C07C 145/00; C07C 149/16
[58] Field of Search ................................ 260/543 H

[56] References Cited
UNITED STATES PATENTS 2,664,442   12/1953   Kamlet ........................... 260/543 H OTHER PUBLICATIONS
Chem. Review vol. 58 pp. 509–512 (1958).

*Primary Examiner*—Lewis Gotts
*Assistant Examiner*—D. R. Phillips
*Attorney, Agent, or Firm*—Pennie & Edmonds

[57] ABSTRACT

Perchloromethyl mercaptan is prepared with about 10% saving in raw materials by an improved process comprising (i) chlorinating carbon disulfide in the presence of iodine to produce a first chlorinated liquor, (ii) separating said liquor by distillation into a high-boiling fraction of technical-grade perchloromethyl mercaptan and a low-boiling fraction, A, (iii) chlorinating fraction A in the presence of iodine and absence of any substantial amount of metallic halides to produce a second chlorinated liquor, (iv) separating said second liquor by distillation into a high boiling fraction of crude perchloromethyl mercaptan and a second low-boiling fraction, B, consisting essentially of sulfur dichloride, and (v) heating fraction B at about 90°–150°C in presence of a metallic halide to form sulfur monochloride and regenerate chlorine.

5 Claims, 5 Drawing Figures

PROCESS FOR PREPARED PERCHLOROMETHYL MERCAPTAN BY CHLORINATION OF CARBON DISULFIDE

The present invention provides an improved process for preparing perchloromethyl mercaptan by chlorination of carbon disulfide. Perchloromethyl mercaptan, $CCl_3SCl$, hereinafter abbreviated as PCMM, is known also as trichloromethanesulfenyl chloride. Reduction of PCMM with stannous chloride or tin and hydrochloric acid produces thiophosgene or thiocarbonyl chloride $CSCl_2$. Both thiophosgene and PCMM itself are commercially useful as raw materials in the production of many organic sulfur compounds. See KIRK-OTHMER, ENCYCLOPEDIA OF CHEMICAL TECHNOLOGY, Second Edition, Volume 4, page 372 (1964); and, for example, U.S. Pat. Nos. 2,553,771; 2,653,155; and 2,713,058.

BACKGROUND OF THE INVENTION

According to the known procedures, PCMM is produced by chlorination of carbon disulfide in the presence of small quantities of iodine, about 0.005 to 2% (based on weight of carbon disulfide) as catalyst, according to the overall reaction I:

$$CS_2 + 3Cl_2 \rightarrow CCl_3SCl + SCl_2 \qquad (I)$$

This reaction theoretically consumes 409 g of carbon disulfide and 1.145 grams of chlorine per kilogram of PCMM formed, corresponding to a molar ratio $Cl_2/CS_2$ equal to 3.0. However, in industrial practice the chlorine is charged in an amount considerably smaller than theoretical, the molar ratio $Cl_2/CS_2$ scarcely exceeding 2.50 in order not to risk destruction of part of the formed PCMM in the following well-known side reactions:

$$CCl_3SCl + Cl_2 \rightarrow CCl_4 + SCl_2 \qquad (II)$$

$$CCl_3SCl + SCl_2 \rightarrow CCl_4 + S_2Cl_2 \qquad (III)$$

Simultaneously reation (IV), forming carbon tetrachloride directly by the action of chlorine and carbon disulfide, can take place, particularly in the presence of light and traces of metallic chlorides:

$$CS_2 + 3Cl_2 \rightarrow CCl_4 + S_2Cl_2 \qquad (IV)$$

The extent of this reaction corresponds to at least 5% of the charged carbon disulfide. After separating the low-boiling products by distillation (preferably at reduced pressure), a minimum of 1.5% of sulfur monochloride remains, being difficult to remove because its boiling point (138°C) is so close to that of PCMM (148°C.)

In practice, then, equation V represents the overall reaction which takes place with at best 95% yield based on carbon disulfide charged:

$$3CS_2 + 7.5Cl_2 \rightarrow 2.5\ CCl_3-SCl + 2.5\ SCl_2 + 0.5\ CS_2 \qquad (V)$$

Under these conditions, the consumption of reactants is raised from theoretical to at least 508 grams of carbon disulfide and 1.188 grams of chlorine per kilogram of technical grade of PCMM, 98.5% pure.

In most of the prior processes, the higher boiling PCMM and sulfur monochloride are isolated by distillation under reduced pressure being delivered at the tail end or foot of the distillation unit while the lower boiling fractions comprising carbon disulfide, sulfur dichloride and carbon tetrachloride are delivered at the head of the distillation unit and are then transformed into a mixture of carbon tetrachloride and sulfur monochloride by chlorination according to the overall equation VI, using a metallic chloride as catalyst:

$$2.5\ SCl_2 + 0.5\ CS_2 + 0.25\ Cl_2 \rightarrow 0.5\ CCl_4 + 1.75\ S_2Cl_2 \qquad (VI)$$

SUMMARY OF THE INVENTION

Present inventor has now surprisingly established that if the above mentioned chlorination of the low-boiling fraction is, in contrast to the usual practice, carried out in the substantially complete absence of such metallic halide catalyst but in the presence, instead, of iodine, the chlorine action takes place according to the overall equation (VII) with the formation of a mixture of PCMM, sulfur monochloride and sulfur dichloride:

$$2.5\ SCl_2 + 0.5\ CS_2 + 1.4\ Cl_2 \rightarrow 0.5\ CCl_3SCl + 0.1\ S_2Cl_2 + 2.8\ SCl_2 \qquad (VII)$$

Present inventor has furthermore ascertained that when the (second) liquor, chlorinated according to equation VII is submitted to distillation under reduced pressure i.e., between 50 to 400 torrs, two fractions can be separated, one being crude PCMM containing about 10–15% sulfur monochloride, the other being very rich in sulfur dichloride but substantially free of carbon disulfide; and that this ("second") low-boiling fraction (i.e., coming from the "second" distillation) decomposes in the presence of a metallic chloride like molybdenum pentachloride at about 90°–150°C to form sulfur monochloride and regenerate chlorine. A combination of these steps in succession has been found to effect an overall saving of about 10% in the raw materials required to make a given total weight of technical grade PCMM.

Briefly stated, the present invention is an improved process for preparing perchloromethyl mercaptan which comprises (i) chlorinating carbon disulfide in the presence of iodine to produce a first chlorinated liquor, (ii) separating said liquor by distillation into a high-boiling fraction of technical grade perchloromethyl mercaptan and a low-boiling fraction, A, (iii) chlorinating fraction A in the presence of iodine and absence of any substantial amount of metallic halides to produce a second chlorinated liquor, (iv) separating said second liquor by distillation into a high-boiling fraction of crude perchloromethyl mercaptan and a second low-boiling fraction, B, comprising sulfur dichloride and (v) heating fraction B at about 90°–150°C in presence of a metallic halide (about 0.5 to 10% of molybdenum pentachloride, or ferric chloride, or tungsten chloride...) to form sulfur monochloride and regenerate chlorine.

This invention also provides for optional steps of processing the crude perchloromethyl mercaptan. According to one embodiment of the invention, the crude PCMM obtained in step (iv) above is reintroduced into the distillation of step (ii). According to an alternative embodiment of the overall process, the crude PCMM from step (iv) is separately purified by chlorination under pressure lower than one bar in the presence of about 100 to 2000 ppm of iodine, based on weight of PCMM. The sulfur dichloride thus formed is then eliminated by distillation to produce a high-purity technical grade of PCMM containing about 96% to 99% by weight of pure PCMM.

DETAILED DESCRIPTION

Figure 1:
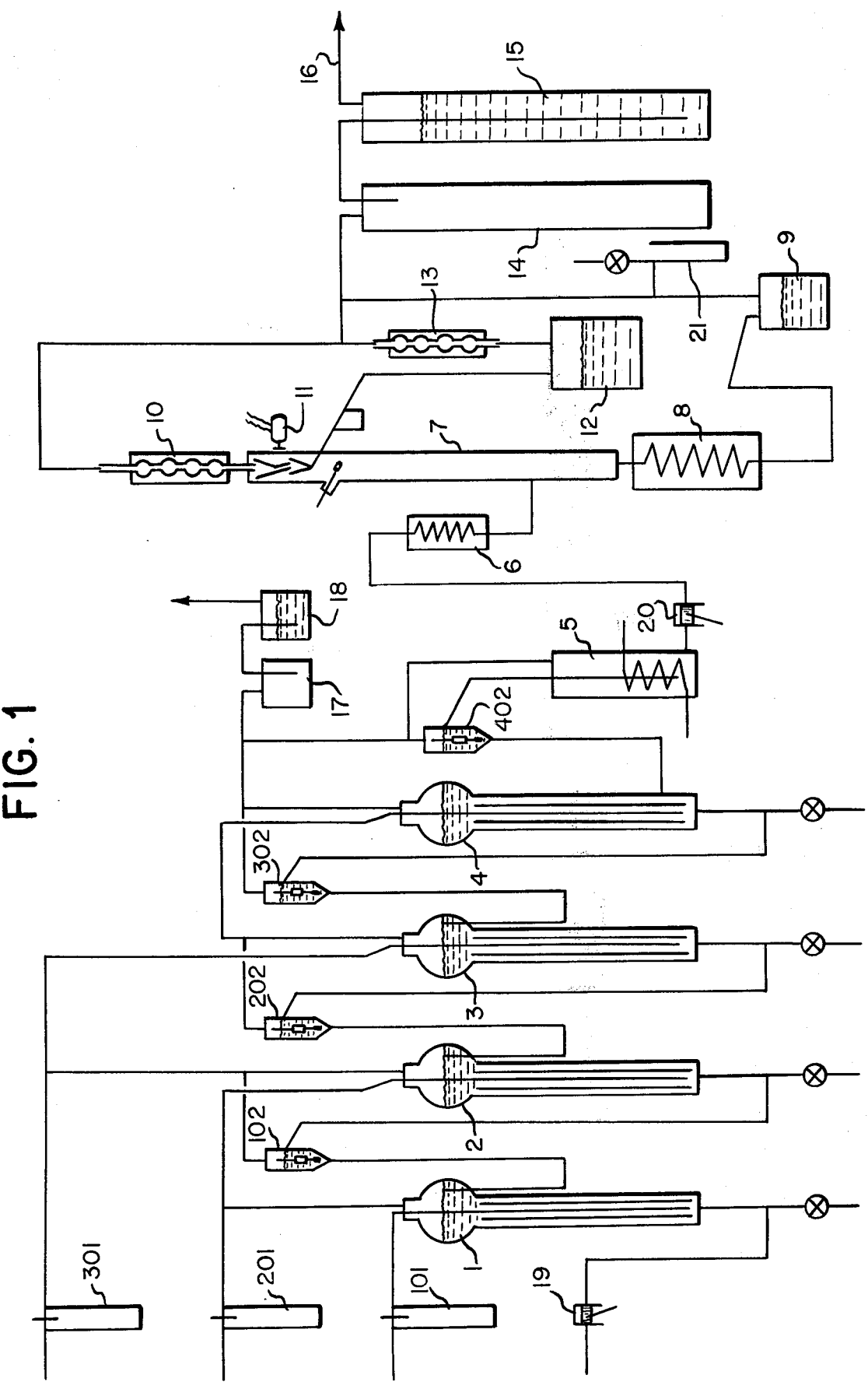

Thus, the instant invention relates to an improvement in the conventional method of preparing PCMM by iodine-catalyzed chlorination of carbon disulfide and separating the formed PCMM by distilling off a low-boiling fraction. In the conventional method, the low-boiling fraction is chlorinated over a metallic chloride catalyst to produce carbon tetrachloride and sulfur monochloride. In the improvement of the instant invention, metallic chlorides are avoided and the same low boiling fraction is chlorinated in the presence of iodine to produce more PCMM. The distillation of this second chlorinated product then yields a crude PCMM and a second low-boiling fraction containing sulfur dichloride which is then converted to a sulfur monochloride by-product and to chlorine which is recycled in the treatment of fresh carbon disulfide.

The quantity of iodine necessary as the catalyst for the chlorination of the first low-boiling fraction in step (iii) on page 5 line 1 (i.e. for reaction VII on page 4 line 10) can vary from about 100 to 2000 ppm, based on total reaction mixture. All or most of the iodine can be the iodine used earlier to catalyze the chlorination of $CS_2$ and recovered in combination with the low-boiling fractions delivered at the head of the distillation unit.

According to the present invention, the products of reaction (VII) are separated from each other by distillation under reduced pressure, with the PCMM residue containing about 10–15% of $S_2Cl_2$ and the new low-boiling fraction, hereinafter identified as the second head-fraction is substantially free of carbon disulfide, but very rich in $SCl_2$ and containing about 10 to 15% of $CCl_4$ — showing that reaction (IV) takes place simultaneously with reaction (VII).

Said second head-fraction can be decomposed with recovery of chlorine according to equation (VIII) at a temperature of about 90–150%C. in a reactor containing as catalyst a small quantity of a metallic chloride, as for example in particular molybdenum pentachloride, ferric chloride, tungsten chloride,

$$2SCl_2 \rightarrow S_2Cl_2 + Cl_2 \quad\quad (VIII)$$

The overall materials balance for the preparation of PCMM according to the improved procedure of the invention corresponds to the sum of equations V, VII and VIII and in overall corresponds to the equation IX:

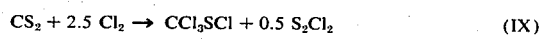

$$CS_2 + 2.5\ Cl_2 \rightarrow CCl_3SCl + 0.5\ S_2Cl_2 \quad\quad (IX)$$

Thus, in spite of the 5 to 7% of $CS_2$ consumed by the "parasitic" side reaction IV, this method achieves the production of 1 kilogram of PCMM with about 430–450 grams of carbon disulfide and about 1.015–1.080 grams of chlorine, corresponding to a saving in required starting materials of about 10% by weight compared to the amounts required in the conventional procedures.

The procedure for preparing PCMM according to the instant invention can be accomplished in discontinuous fashion or, particularly in the case of installations having large capacity, it is advantageous to set up the process continuously, carrying out in successive steps a multistage chlorination of carbon disulfide, a distillation under reduced pressure drawing off the technical grade PCMM obtained, the chlorination of the head-fraction i.e. low-boiling fraction followed by separation by distillation under reduced pressure of the PCMM obtained in this chlorination and recycling this PCMM in the first distillation column from the second head-fraction, and decomposing by heat of the $SCl_2$ in this second head-fraction with recovery of chlorine and reintroduction of said chlorine into the first cycle of chlorination and formation of sulfur monochloride $S_2Cl_2$.

Figure 2:
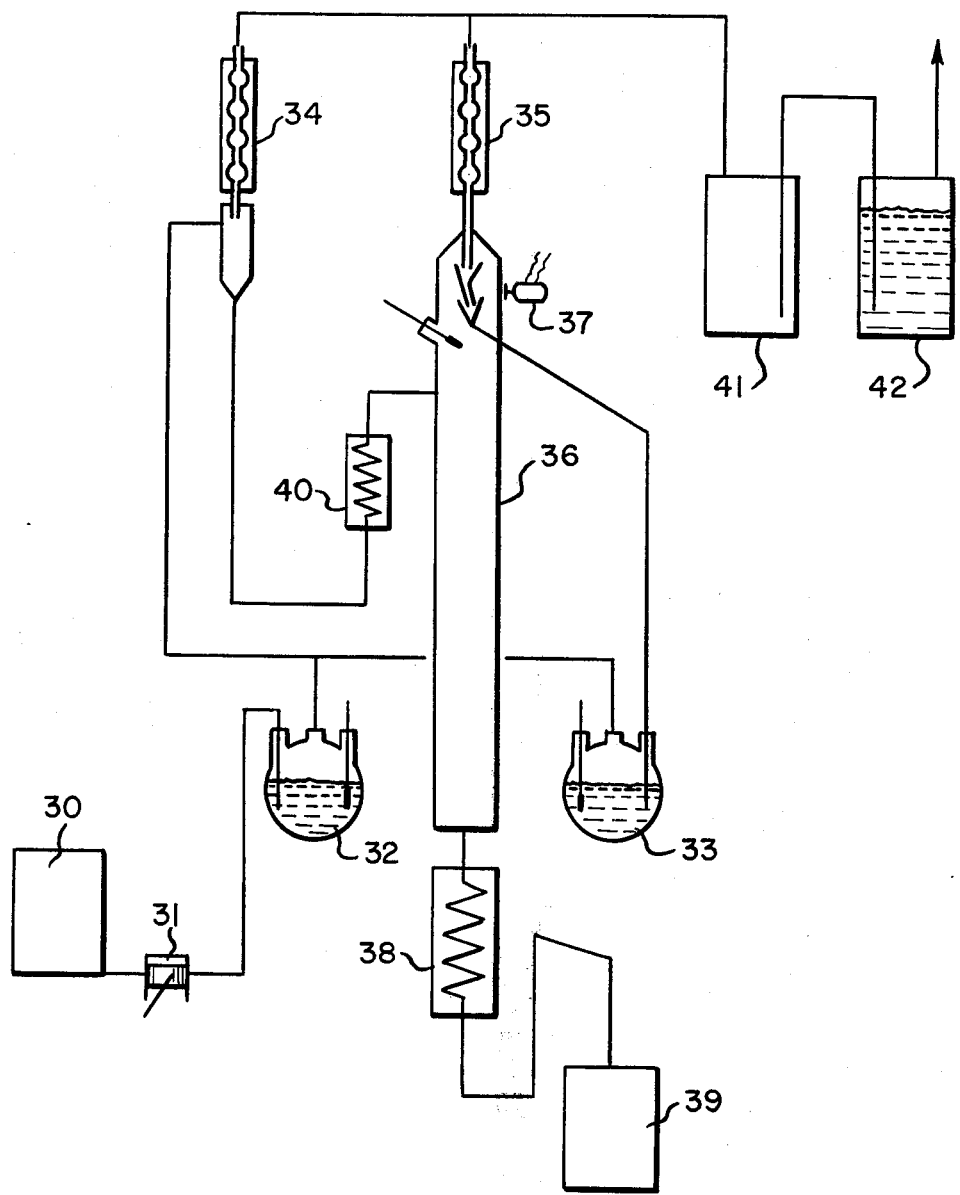

The following examples illustrate modifications of the present invention in non-limiting fashion, using equipment described schematically in FIGS. 1 and 2.

The equipment of FIG. 1 includes three tubular chlorinators 1, 2 and 3, provided with cooling jackets and a "ripener" or finishing-off reactor 4 for the purpose of effecting the reaction of some 3 or 4% with $CS_2$ which has not reacted in the three chlorinators as well as effecting the reaction of $SCl_2$ on the residual $CS_2$ in order to augment the yield of PCMM.

The flowmeters 101, 201 and 301 provide means of observing the flow rates of chlorine delivered respectively to chlorinators 1, 2 and 3 while gauges 102, 202, 302 and 402 permit observation by means of densimeters of the density of the respective chlorination liquors, thus permitting control of the degree of chlorination.

A volumetric pump 19, receives from a storage vessel carbon disulfide containing about 0.08% by weight iodine and supplies it to chlorinator 1 at a rate corresponding to the flow rate of chlorine through 101. The small portion of this chlorine which remains unreacted in 1 is mixed with an amount of chlorine measured at 201 for the purpose of injecting into chlorinator 2. The counter pressure of the bubbling chlorine contributes to cause the liquor to rise in the equilibrated gauge 102; in like manner the liquor is adjusted at chlorinator 3 and at the finishing-off reactor 4 which work under pressure which diminishes up to the trap 17 and absorber 18 filled with 20% aqueous caustic soda solution to catch the last traces of chlorine issuing from the liquid contained in 402 and from the refrigerated liquid in intermediate storage tank 5.

A volumetric pump 20 sends the chlorinated liquor into an evaporator 6 heated to 70° by circulation of hot water controlled by a thermostat which is not shown. The partially vaporized liquor is directed to distillation column 7 furnished with helicoid packing rings of 5 mm. dimension. The foot of this column comprises a helix shaped tube 8 having diameter 10 mm and heated at 120° by a thermostat jacket. This tube serves as exhaust still, while the PCMM flows out into vessel 9. Column 7 is fitted at the top with a reflux condenser 10 cooled by circulating brine at −20°C and contains a magnetic head 11 activited by a thermocouple which assures that the desired composition is drawn off from the head into vessel 12 fitted with a brine-cooled reflux condenser 13.

The small quantity of chlorine which has not reacted passes over to the trap 14 and to the absorber 15 containing aqueous sodium hydroxide solution, is connected with an evacuated pipe system 16 leading through an aspirator into water. A system regulating the vacuum is not shown in the picture. A mercury manometer 21 protected from a small reentry of air effects control of the working pressure of the distillation.

This invention will be further illustrated by description in connection with the following specific examples of the practice of it wherein, as also elsewhere herein, proportions are in parts by weight unless stated otherwise.

EXAMPLE 1

By means of pump 19 there is injected into chlorinator 1 152 grams/hr. of carbon disulfide containing 0.14 grams of iodine and by means of flowmeter 101, 232 grams/hr. of chlorine.

The outlet 102 from chlorinator 1 is directed toward the chlorinator 2 which is fed through 201 with 108 grams/hr. of chlorine while its outlet 202 in turn is directed toward the chlorinator 3 fed through 301 with 27 grams/hr. of chlorine.

The "finishing-off" reactor 4 absorbs completely the few grams of chlorine leaving chlorinator 3 whereby the few percent of chlorine dissolved in the liquor complete the reaction of the excess carbon disulfide to form PCMM. The density in 402 reaches 1.616 whereas in 302 it is only 1.602. The liquor contained in the storage vessel 5 cooled at −5°C contains 52.7%, by weight, of PCMM, 5.5% of carbon disulfide and 4.5% of carbon tetrachloride, the remaining costituents being chlorides of sulfur.

The volumetric flowrate of pump 20 is substantially 2.75 times that of pump 19 and is regulated in a manner such as to maintain the level in 5 substantially constant. The liquid is sent to the evaporator 6 which vaporizes practically all the low-boiling substances, except PCMM which goes into the bottom outlet portion of column 7 then into the reboiling still 8. The switching-thermometer set at 28°C activates the magnetic head 19 which controls the flow so that a part of the head vapors flows back into column 7 and part is drawn off continuously to the receiving vessel 12. The condensers 10 and 13 cooled with brine at −20°C trap the lighter (lower boiling) constituents ($CS_2$ and $SCl_2$) but permit part of the chlorine to escape toward absorber 15. The vacuum is regulated at 16 in a manner such as to have a 200 torrs reading on manometer 21. Over a course of about 100 hours, a PCMM product is withdrawn at an average rate of 280 grams per hour and containing 2.5% by weight sulfur monochloride and less than 1000 ppm of "light" (i.e., low-boiling) impurities including $CS_2$ and $SCl_2$ and $CCl_4$. At the head of the distillation column a stream of average rate 239 grams/hr. is delivered containing, by weight, 12% of carbon disulfide, 72.5% sulfur dichloride and 9.7% carbon tetrachloride.

The mixture of light materials is then pumped by 19 at a flowrate of 478 grams/hr. and led into chlorinator 1 which is also supplied with 90 grams/hr. of chlorine. After passing through chlorinator 1, the mixture is directed in usual manner to chlorinator 2 via 102 together with 21 grams/hr. of chlorine. Successively the stream is likewise directed via 202, 302 and 402 while 17 grams/hr. of chlorine is added at chlorinator 3. The liquor collected at 5 contains, by weight, 0.58% of $CS_2$, 3.07% of $S_2Cl_2$ and 19.7% of PCMM, the remainder being sulfur dichloride. The distillation of this liquor in column 7 supplied through pump 20 furnishes 137.7 grams/hr. of a PCMM product containing 13.5% sulfur monochloride and 467 grams/hr. of "light" substances (called "heads from second distillation") ) containing 0.75% of $CS_2$, 12% $CCl_4$ and 84.7% of $SCl_2$ by weight.

In a filter flask of 3 liter capacity, there is collected the daily production, 3.300 kg. of PCMM recovered in the manner described in the preceding. In this liquid there is dissolved 0.75 grams of iodine and, with cooling to 20°C, 310 grams of chlorine is injected until the pressure reaches 0.4 bars. After about 12 hours contact, the 445 grams of $S_2Cl_2$ contained in the PCMM are substantially completely chlorinated to $SCl_2$ and 3.7% of $CCl_4$ is formed. The chlorine pressure falls back to zero. The 3.61 kg of PCMM thus obtained is charged into the storage vessel 5 and pumped at the rate of 300 grams/hr. to the evaporator 6 and column 7 under a vacuum of 200 torrs. The still 8 delivers to 9 2.74 kg. of PCMM of 99.05% purity which analysis shows to contain 0.85% of $S_2Cl_2$ and the low-boiling fraction contains 16.5% of $CCl_4$ and $SCl_2$ which can be added to the low-boiling fraction delivered during the second distillation.

EXAMPLE 2

The low-boiling fraction from the so-called "second distillation" containing 2.35% of dissolved chlorine, 0.7% of $CS_2$, 84.4% of $SCl_2$ and 12.55% of $CCl_4$ and stored in receptacle 30 of FIG. 2, is pumped by means of pump 31 at a flow rate of 150 grams/hr. toward the spherical flask 32 containing 150 grams of helicoid coils of iron wire for the purpose of decomposing any traces of PCMM and also to facilitate the chlorination of carbon disulfide to sulfur monochloride and carbon tetrachloride.

Although the exothermic reaction starts off spontaneously, the flask 32 is heated to 110°C so as to evaporate substantially all the sulfur monochloride formed by chlorintion of $CS_2$ and by the partial decomposition of $SCl_2$ according to the equilibrium equation $$2\ SCl_2 \rightleftarrows S_2Cl_2 + Cl_2 \qquad (X).$$

The vapors leaving flask 32 are directed to the reflux condenser 34 which permits the formed chlorine to escape to the trap bottle 41 and the absorber 42 previously filled with aqueous 20% sodium hydroxide solution. The vapors condensed at 34 are again evaporated at 40 to be led to the distillation column 36. The latter has at its top the reflux condenser 35 and a magnetic rocking lever 37 which acts to send condensate particularly rich in $SCl_2$ to the spherical flask 33 which serves as a decomposer, containing 10 grams of molybdenum pentachloride catalyst to favor reaction X in the left-to-right direction. As a result of the presence of $CCl_4$ in the reflux at 37 an equilibrium temperature is established at about 90°C which maintains the decomposer at a level substantially constant. The vapors leaving the decomposer 33 are composed of chlorine, $SCl_2$ remaining from incomplete reaction, $CCl_4$ and $S_2Cl_2$. These vapors are combined with those from the flask 32 in order to be treated jointly.

The foot of column 36 consists of a still 38 heated at 110°–120°C, from which escapes to 39 118 grams/hr. of high-boiling ("heavy") residue containing again 9% $SCl_2$, 19% $CCl_4$ and 72% $S_2Cl_2$. This mixture is distilled intermittently under reduced pressure of 200 torrs thus effecting the separation of a 99.8% pure fraction of $CCl_4$ containing 400 ppm of sulfur derivatives, expressed as weight of sulfur per total product. The treatment of this $CCl_4$ with a 20% solution of caustic soda or with Javelle water containing 12% active chlorine furnishes a product having only 2 ppm of sulfur which is suitable for many applications.

What is claimed is:
1. An improved process for preparing perchloromethyl mercaptan which comprises (i) chlorinating carbon disulfide in the presence of iodine to produce a first chlorinated liquor, (ii) separating said liquor by distillation into a high-boiling fraction of technical grade perchloromethyl mercaptan and a low-boiling fraction, A (iii) chlorinating fraction A in the presence of iodine and absence of any substantial amount of metallic halides to produce a second chlorinated liquor, (iv) separating said second liquor by distillation into a high-boiling fraction of crude perchloromethyl mercaptan and a second low-boiling fraction, B, comprising sulfur dichloride and (v) heating fraction B at about 90°–150°C in presence of a metallic halide to form sulfur monochloride and regenerate chlorine.

2. Process of claim 1 wherein the crudee perchloromethyl mercaptan obtained in step (iv) is reintroduced into the distillation of step (ii), thus increasing the yield of technical grade perchloromethyl mercaptan in step (ii).

3. Process of claim 1 wherein the crude perchloromethyl mercaptan obtained in step (iv) is chlorinated in the presence of iodine and the resultant chlorinated product is separated by distillation into sulfur dichloride and technical grade perchloromethyl mercaptan.

4. Process of claim 1 wherein heating step (v) is carried out in the presence of molybdenum pentachloride.

5. Process of claim 1 carried out continuously.

* * * * *